United States Patent [19]

Yamasaka et al.

[11] Patent Number: 5,294,439
[45] Date of Patent: Mar. 15, 1994

[54] STABILIZED BENZIMIDAZOLE DERIVATIVE AND COMPOSITION

[75] Inventors: Heinojo Yamasaka, Ushiku; Hiroyasu Uchiyama, Koshigaya; Hirotaka Masuda, Sakura; Yoshiomi Sakamoto, Oyama; Yoshimi Nakamigawa, Sekijo; Mitsuko Yoshioka, Yoshikawa; Terumasa Moriga, Misato, all of Japan

[73] Assignee: Nippon Chemiphar Co., Ltd., Tokyo, Japan

[21] Appl. No.: 379,256

[22] Filed: Jul. 13, 1989

Related U.S. Application Data

[63] Continuation of Ser. No. 56,757, Jun. 2, 1987, abandoned.

[30] Foreign Application Priority Data

Jun. 2, 1986 [JP] Japan .................. 61-128988
Jun. 2, 1986 [JP] Japan .................. 61-128989
Jul. 8, 1986 [JP] Japan .................. 61-160612

[51] Int. Cl.$^5$ .................. A61K 31/41; A61K 31/415; A61K 31/74
[52] U.S. Cl. .................. 424/78.01; 424/451; 424/452; 424/456; 424/463; 424/464; 424/465; 424/474; 424/480; 424/485; 424/486; 514/212; 514/338; 514/395; 540/603; 548/307.1; 546/199
[58] Field of Search .................. 548/329; 546/199; 540/603; 514/212, 338, 395; 424/78.01, 451, 452, 456, 463, 464, 465, 474, 480, 485, 486

[56] References Cited

FOREIGN PATENT DOCUMENTS 2161160 6/1985 United Kingdom .................. 548/329
2163747 5/1986 United Kingdom .................. 548/329

OTHER PUBLICATIONS

Ritschel. Applied biopharmacy, pp. 293-303 (1973).

Primary Examiner—Johann Richter
Attorney, Agent, or Firm—Sixbey, Friedman, Leedom & Ferguson

[57] ABSTRACT

A stabilized physiologically active benzimidazole derivative having the formula (I):

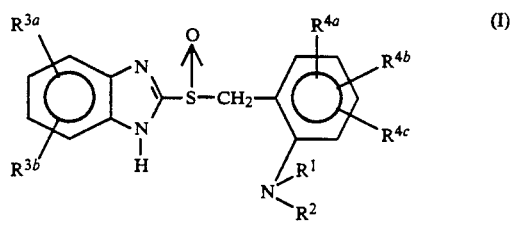

wherein $R^1$ is hydrogen atom, an alkyl group having 1 to 8 carbon atoms, a fluoroalkyl group having 1 to 6 carbon atoms, a cycloalkyl group, phenyl group or an aralkyl group, $R^2$ is hydrogen atom or a lower alkyl group, or $R^1$ and $R^2$ together with the adjacent nitrogen atom form a ring, and each of $R^{3a}$, $R^{3b}$, $R^{4a}$, $R^{4b}$ and $R^{4c}$ independently is hydrogen atom, a halogen atom, a fluoroalkyl group having 1 to 6 carbon atoms, a lower alkyl group, a lower alkoxy group, a lower alkoxycarbonyl group or an amino group. The stabilized benzimidazole derivative is in amorphous form or present in contact with a basic material.

5 Claims, No Drawings

STABILIZED BENZIMIDAZOLE DERIVATIVE AND COMPOSITION

This application is a continuation of Ser. No. 07/056,757, filed Jun. 2, 1987, now abandoned.

BACKGROUND OF THE INVENTION

1. Field of the Invention

This invention relates to a stabilized benzimidazole derivative and a composition in which a benzimidazole derivative is stabilized.

2. Description of the Prior Art

There is known a physiologically active benzimidazole derivative having the formula (I):

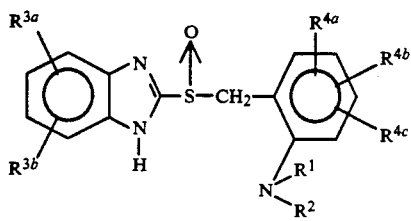

wherein $R^1$ is hydrogen atom, an alkyl group having 1 to 8 carbon atoms, a fluoroalkyl group having 1 to 6 carbon atoms, a cycloalkyl group, phenyl group or an aralkyl group, $R^2$ is hydrogen atom or a lower alkyl group, or $R^1$ and $R^2$ together with the adjacent nitrogen atom form a ring, and each of $R^{3a}$, $R^{3b}$, $R^{4a}$, $R^{4b}$ and $R^{4c}$ independently is hydrogen atom, a halogen atom, a fluoroalkyl group having 1 to 6 carbon atoms, a lower alkyl group, a lower alkoxy group, a lower alkoxycarbonyl group or an amino group.

The benzimidazole derivative of the formula (I) shows a prominent inhibitory action on secretion of gastric acid as is described in GB 2,161,160A and GB 2,163,747A (corresponding to DE 3,531,487A1). Moreover, some benzimidazole derivatives of the formula (I) can be employed as cytoprotective agents for gastrointestinal tract.

SUMMARY OF THE INVENTION

The present inventors have made study for acturally utilizing the benzimidazole derivative of the formula (I) as a physiologically active component of a pharmaceutical and found that these benzimidazole derivative is poor in storage stability.

Accordingly, an object of the present invention is to provide a physiologically active benzimidazole derivative of the formula (I) which is improved in storage stability.

Another object of the invention is provide a composition containing a physiologically active benzimidazole derivative under stabilized condition.

There is provided by the present invention a physiologically active benzimidazole derivative having the formula (I):

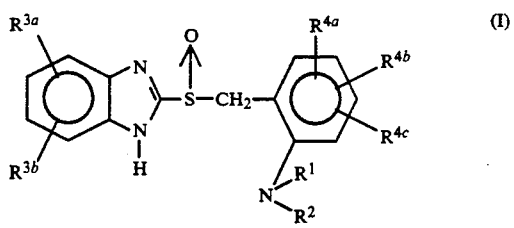

wherein $R^1$ is hydrogen atom, an alkyl group having 1 to 8 carbon atoms, a fluoroalkyl group having 1 to 6 carbon atoms, a cycloalkyl group, phenyl group or an aralkyl group, $R^2$ is hydrogen atom or a lower alkyl group, or $R^1$ and $R^2$ together with the adjacent nitrogen atom form a ring, and each of $R^{3a}$, $R^{3b}$, $R^{4a}$, $R^{4b}$ and $R^{4c}$ independently is hydrogen atom, a halogen atom, a flouroalkyl group having 1 to 6 carbon atoms, a lower alkyl group, a lower alkoxy group, a lower alkoxycarbonyl group or an amino group, which is in amorphous state or is kept in contact with an organic or inorganic basic material.

Particularly, the present invention provides a stabilized physiologically active benzimidazole derivative of the formula (II):

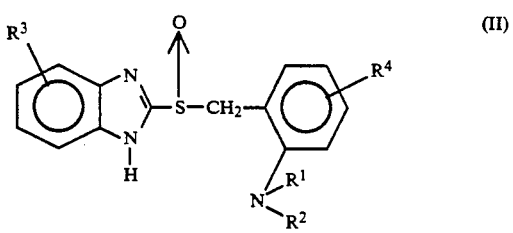

wherein $R^1$ is hydrogen atom, an alkyl group having 1 to 8 carbon atoms, a cycloalkyl group, phenyl group or an aralkyl group, $R^2$ is hydrogen atom or a lower alkyl group, or $R^1$ and $R^2$ together with the adjacent nitrogen atom form a ring, and each of $R^3$ and $R^4$ independently is hydrogen atom, a halogen atom, trifluoromethyl group, a lower alkyl group, a lower alkoxy group, a lower alkoxycarbonyl group or an amino group, which is in amorphous state or is kept in contact with an organic or inorganic basic material.

DETAILED DESCRIPTION OF THE INVENTION

The benzimidazole derivatives of the formula (I) can be prepared by known processes. For instance, the benzimidazole derivative of the formula (II) can be prepared by the process according to the following equation:

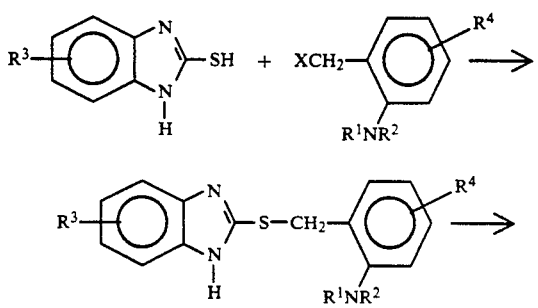

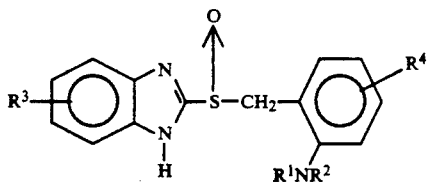

wherein X is a reactive group and each of $R^1$, $R^2$, $R^3$ and $R^4$ has the same meaning as defined hereinbefore. The benzimidazole derivatives of the formula (I) other than the derivative of the formula (II) can be prepared in similar manners.

Representative examples of the compounds of the formula (I) include:

Compound 1: 2-(2-dimethylaminobenzylsulfinyl)benzimidazole,
Compound 2: 2-(2-diethylaminobenzylsulfinyl)benzimidazole,
Compound 3: 2-(2-aminobenzylsulfinyl)benzimidazole,
Compound 4: 2-(2-methylaminobenzylsulfinyl)benzimidazole,
Compound 5: 2-(2-dimethylaminobenzylsulfinyl)-5-methoxybenzimidazole,
Compound 6: 2-(2-diethylaminobenzylsulfinyl)-5-methoxybenzimidazole,
Compound 7: 2-(2-dimethylamino-6-methylbenzylsulfinyl)benzimidazole,
Compound 8: 2-(2-dimethylaminobenzylsulfinyl)-5-methoxycarbonylbenzimidazole,
Compound 9: 2-(2-dimethylaminobenzylsulfinyl)-5-methylbenzimidazole,
Compound 10: 5-chloro-(2-dimethylaminobenzylsulfinyl)benzimidazole,
Compound 11: 5-amino-(2-dimethylaminobenzylsulfinyl)benzimidazole,
Compound 12: 2-(2-dimethylamino-5-methoxybenzylsulfinyl)benzimidazole,
Compound 13: 2-(2-dimethylamino-5-methylbenzylsulfinyl)benzimidazole,
Compound 14: 2-(2-piperidinobenzylsulfinyl)benzimidazole,
Compound 15: 2-[2-(N-cyclohexyl-N-methylamino)-benzylsulfinyl]benzimidazole, and
Compound 16: 2-[2-(N-benzyl-N-methylamino)benzylsulfinyl]benzimidazole.

The benzimidazole derivative employed in the present invention preferably is a compound having the formula (I) wherein $R^1$ is an alkyl group containing 1-8 carbon atoms. $R^2$ preferably is a lower alkyl group. Preferably, each of $R^{3a}$ and $R^{3b}$ is independently hydrogen atom or an alkoxy group. Preferably, each of $R^{4a}$, $R^{4b}$ and $R^{4c}$ is independently is hydrogen atom or a lower alkyl group. In the specification, the lower alkyl group and the lower alkoxy group mean those containing 1-6 carbon atoms.

As a result of the study of the present inventors, it has found that the benzimidazole derivative of the formula (I), which is prepared in the form of crystals according to known processes for the preparation, can be prominently improved in storage stability when it is formed in amorphous state.

The benzimidazole derivative of the formula (I) can be converted into a amorphous compound, for instance, by freezing a crystalline compound in an organic solvent and then evaporating the solvent. However, it is advantageous to treat the crystalline compound in such a manner that the crystalline compound is dissolved in an organic solvent containing an organic polymer and then forcing to remove the solvent through evaporation or that the crystalline compound is dissolved in an organic solvent containing an organic polymer and then spray-drying the resulting solution.

In the above process, there is no need of dissolving the benzimidazole derivative and/or the organic polymer in the solvent. For instance, the benzimidazole derivative and/or organic polymer can be suspended in the organic solvent. For this reason, the organic solvent can be replaced with an aqueous organic solvent or replaced simply with water. In the case that water or an aqueous organic solvent is employed as the solvent, the organic polymer preferably is water-soluble. Further, in the case that water or an aqueous organic solvent is utilized, a surface active agent can be utilized as a dispersant.

Examples of the organic polymers employable for converting a crystalline benzimidazole derivative into an amorphous benzimidazole derivative include synthetic or natural polymers such as hydroxypropylcellulose, hydroxypropylmethylcellulose, methylcellulose, ethylcellulose, carboxymethylcellulose sodium, poly(vinylpyrrolidone), poly(vinyl alcohol), poly(sodium acrylate), sodium alginate, gelatin, gum arabic, α-starch, oxidized starch, heat-treated starch, enzyme-treated starch, agar and α-cyclodextrin. Preferred are cellulose derivatives.

As described above, the organic polymer preferably is a water soluble polymer in the case the solvent is water or an aqueous organic solvent. Examples of the water-soluble polymers include carboxymethylcellulose sodium, poly(vinyl alcohol), poly(sodium acrylate), sodium alginate, gelatin, gum arabic, α-starch, oxidized starch, heat-treated starch, enzyme-treated starch, and agar.

The organic polymer is preferably utilized in an amount of not less than 0.5 time, more preferably not less than 2 times as much as a weight of the benzimidazole derivative.

There is no limitation with respect to the organic solvent employed for the prepareation of a solution of the benzimidazole derivative and the organic polymer, so long as the derivative and the polymer are dissolved in the solvent. Advantageously employable are alcohols and halogenated alkyls. As described above, the organic solvent can be used in combination with water and optionally with a surface active agent.

It is not known why the benzimidazole derivatives of the formula (I) are prominently improved in the storage stability by converting a crystalline product into an amorphous product. However, it can be thought as follows.

It is observed that the benzimidazole derivative of the formula (I) emits strong heat when it decomposes. Accordingly, it is assumed that when the benzimidazole derivative in crystalline state once starts decomposition locally at a certain area, decomposition is extended rapidly to other area by way of heat produced by the strong exothermic reaction. In amorphous state, the local decomposition of the benzimidazole derivative is extended slowly to other area because the produced heat is not transmitted to the surrounding area rapidly.

It is further assumed that the organic polymer introduced into the benzimidazole derivative composition serves for forcing the formation of an amorphous compound in the conversion procedure and further serves in the composition as a barrier between the resulting amorphous particles for suppressing transmission of heat from the decomposed area to other area, whereby further improving the storage stability of the benzimidazole derivative.

According to the present invention, the improvement of storage stability of the benzimidazole derivative of the formula (I) can be accomplished by bringing the derivative into contact withand a basic material in an amount of not less than 5 weight %, preferably not less than 10 weight %, more preferably in the range of 10 to 200 weight %, based on an amount of the benzimidazole derivative. For instance, the contact between the benzimidazole derivative and the basic material can be attained by preparing a composition containing both the benzimidazole derivative and the basic material.

The basic material used herein means a material which shows pH 7 or higher, preferably pH 8 or higher, in the form of an aqueous solution or an aqueous suspension.

The basic material preferably is a hydroxide or a salt with a weak inorganic acid of a metal such as an alkali metal, an alkaline earth metal and aluminum. More concretely, the basic material preferably is a hydroxide such as alumina magnesium hydroxide (2.5 $Al_2O_3.Mg(OH)_2$), aluminum hydroxide and magnesium hydroxide. Examples of the salts with a weak inorganic acid include carbonates such as potassium carbonate, calcium carbonate, sodium hydrogen carbonate and magnesium carbonate; phosphates such as potassium monohydrogen phosphate, potassium phosphate and sodium phosphate; and coprecipitation products of hydroxide with carbonate such as aluminum hydroxide-sodium hydrogen carbonate coprecipitation product and aluminum hydroxide-magnesium carbonate-calcium carbonate coprecipitation product.

The basic material may be a salt of an organic acid (e.g., higher fatty acid) with an alkali metal, an alkaline earth metal, aluminum and amine. The basic material may be an amide, a basic amino acid, a thiamine and an amine. Examples of the organic acids are fatty acids having 12-22 carbon atoms, benzoic acid, alginic acid, edetic acid (EDTA), citric acid, glycyrrhizinic acid, glutamic acid, gluconic acid, succinic acid, fumaric acid, salicylic acid, and lactic acid. Preferred are higher fatty acids having 12-22 carbon atoms such as stearic acid, palmitic acid and myristic acid. Examples of the metals, include sodium, potassium, calcium, magnesium, and aluminum. Examples of the amines include isopropanolamine, diphenylamine, ethanolamine, and benzylamine.

Preferred salts of organic acids with an alkali metal, an alkaline earth metal and aluminum are sodium stearate, potassium stearate, magnesium stearate, aluminum stearate, sodium palmitate, potassium palmitate, magnesium palmitate, aluminum palmitate, sodium myristate, potassium myristate, magnesium myristate, aluminum myristate, sodium benzoate, sodium alginate, sodium edetate, sodium citrate, sodium glycirrhizinate potassium glycillycinate, sodium glutamate, sodium gluconate, potassium gluconate, sodium succinate, sodium fumarate, sodium salicyate, and calcium lactate.

Examples of the amides include nicotinic amide and monomethylnicotinic amide. An example of the basic amino acid is hystidine. An example of the thiamine is vitamine $B_1$. Examples of the amines include diisopropanolamine, diphenylamine, ethanolamine and benzylamine.

In the composition containing both the benzimidazole derivative of the formula (I) and a basic material, the benzimidazole derivative preferably is present in the form of particles preferably having a mean diameter of not more than 10 μm. The benzimidazole derivative of the formula (I) is more stable when it is in the form of such fine particles.

The benzimidazole derivative can be converted into fine particles using known micronizers for the preparation of fine particles. Examples of such micronizers include mechanical micronizers such as pin mill, attrition mill, screw crusher, ring roller mill, ball mill; and hydromechanical energy micronizers such as jet mill, jet pulverizer, micronizer, reductionizer jet pulverizer and air mill.

The stabilized amorphous benzimidazole derivative and the composition of the stabilized benzimidazole derivative shows prominent inhibitory action on secretion of gastric acid and also is employable as a cytoprotective agent for gastrointestinal tract. The stabilized benzimidazole derivative of the formula (I) and the composition containing the stabilized benzimidazole derivative can be administered orally or parenterally. Examples of the preparation forms for oral administration include tablets, capsules, powder, granules, and syrup. In the formulation of these preparations, there can be used excipients, disintegrants, binders, lubricants, pigments, diluents and the like which are commonly used in the art. Examples of the excipients include glucose, sucrose, lactose, and microcrystalline cellulose. Examples of the disintegrants include starch and carboxymethylcellulose calcium. Examples of the lubricants include hardened oil and talc. Examples of the binders include hydroxypropylcellulose, gelatin and polyvinylpyrrolidone. Other additives can be also used.

The dose is generally not more than 500 mg/day, preferably about 100 μg/day to 300 mg/day, for an adult. This value is expressed in terms of the amount of the physiologically active compound, namely the benzimidazole derivative of the formula (I). The dose can be either increased or decreased depending upon the age and other conditions.

The present invention is further described by the following examples.

Synthesis of 2-(2-Dimethylaminobenzylsulfinyl)benzimidazole (1) 2-(2-Dimethylaminobenzylthio)benzimidazole:

2-Mercaptobenzimidazole (4.73 g) was dissolved in 150 ml of ethanol, and to the solution was added 6.18 g of 2-dimethylaminobenzyl chloride hydrochloride. The mixture was stirred at room temperature for 30 minutes. Precipitated crystals were collected by filtration. A saturated aqueous $NaHCO_3$ solution was added to the crystals, and the resulting mixture was extracted with chloroform. The chloroform layer was washed with saturated brine and then dried over anhydrous sodium sulfate. The solvent was distilled off under reduced pressure and the residue was recrystallized from a mixture of chloroform and acetonitrile to obtain 5.39 g of 2-(2-dimethylaminobenzylthio)benzimidazole as a colorless crystalline product (m.p. 164° C.).

(2) 2-(2-Dimethylaminobenzylsulfinyl)benzimidazole
2-(2-Dimethylaminobenzylthio)benzimidazole (4.8 g) was dissolved in a mixture of 40 ml of chloroform and 5 ml of methanol. After the solution was chilled to 0° C., 3.86 g of m-chloroperbenzoic acid (purity: 70%) was added portionwise. Ten minutes later, a saturated aqueous NaHCO$_3$ solution was added to the reaction mixture, and the resulting mixture was extracted with chloroform. The chloroform solution was washed with saturated brine and then dried over anhydrous sodium sulfate. The chloroform was distilled off under reduced pressure and the residue was recrystallized from a mixture of chloroform and ether to obtain 2.97 g of 2-(2-dimethylaminobenzylsulfinyl)benzimidazole as a colorless crystalline product (m.p. 116° C., decomposed).

EXAMPLE 1

In 10 ml of methyl alcohol were dissolved 1.0 g of the colorless 2-(2-dimethylaminobenzylsulfinyl)benzimidazole and 3.0 g of hydroxypropylcellulose. The resulting solution was placed in a rotary evaporator for concentration. The concentrated residue was poured in a Petri dish, and placed overnight in a vacuum dryer at 35° C. The dried composition product was in the form of a pale yellow film.

The composition in the form of a film was analyzed by X-ray diffraction. No diffraction pattern was observed. Accordingly, it was confirmed that the 2-(2-dimethylaminobenzylsulfinyl)benzimidazole in the composition was in amorphous state.

EXAMPLE 2

In 100 ml of chloroform were dissolved 3.0 g of the colorless 2-(2-dimethylaminobenzylsulfinyl)benzimidazole and 9.0 g of poly(vinylpyrrolidone). The resulting solution was spray dried using a minispray dryer (manufactured by Yamato Kagaku Co., Ltd., Japan) at a spraying rate of 3.5 ml/min. and a temperature of supplied air at 100° C., to obtain a fine powdery composition.

The powdery composition was analyzed by X-ray diffraction. No diffraction pattern was observed. Accordingly, it was confirmed that the 2-(2-dimethylaminobenzylsulfinyl)benzimidazole in the composition was in amorphous state.

EXAMPLE 3

The procedure of Example 2 was repeated except for replacing the poly(vinylpyrrolidone) with the same amount of hydroxypropylcellulose to obtain a fine powdery composition.

The powdery composition was analyzed by X-ray diffraction. No diffraction pattern was observed. Accordingly, it was confirmed that the 2-(2-dimethylaminobenzylsulfinyl)benzimidazole in the composition was in amorphous state.

EXAMPLE 4

The procedure of Example 2 was repeated except for replacing the poly(vinylpyrrolidone) with the same amount of hydroxypropylmethylcellulose to obtain a fine powdery composition.

The powdery composition was analyzed by X-ray diffraction. No diffraction pattern was observed. Accordingly, it was confirmed that the 2-(2-dimethylaminobenzylsulfinyl)benzimidazole in the composition was in amorphous state.

EXAMPLE 5

The procedure of Example 2 was repeated except for replacing the poly(vinylpyrrolidone) with the same amount of methylcellulose to obtain a fine powdery composition.

The powdery composition was analyzed by X-ray diffraction. No diffraction pattern was observed. Accordingly, it was confirmed that the 2-(2-dimethylaminobenzylsulfinyl)benzimidazole in the composition was in amorphous state.

EXAMPLE 6

In 30 ml of methylene chloride were dissolved 1.0 g of the colorless 2-(2-dimethylaminobenzylsulfinyl)benzimidazole and 1.0 g of a nonionic surface active agent (low HLB type) to obtain an oily solution. Independently, in 250 ml of water were dissolved 3.0 g of carboxymethylcellulose sodium and 1.0 g of a nonionic surface active agent (high HLB type) to obtain an aqueous solution.

The oily solution and the aqueous solution were combined and violently mixed to give an emulsion. The resulting emulsion was spray dried using a minispray dryer (manufactured by Yamato Kagaku Co., Ltd., Japan) at a spraying rate of 2.0 ml/min. and a temperature of supplied air at 120° C., to obtain a fine powdery composition.

The powdery composition was analyzed by X-ray diffraction. No diffraction pattern was observed. Accordingly, it was confirmed that the 2-(2-dimethylaminobenzylsulfinyl)benzimidazole in the composition was in amorphous state.

COMPARISON EXAMPLE 1

In a mortar were mixed 1.0 g of the colorless 2-(2-dimethylaminobenzylsulfinyl)benzimidazole and 3.0 g of hydroxypropylcellulose to obtain a fine powdery composition.

The powdery composition was analyzed by X-ray diffraction. A diffraction pattern was observed. Accordingly, it was confirmed that the 2-(2-dimethylaminobenzylsulfinyl)benzimidazole in the composition was in crystalline state.

COMPARISON EXAMPLE 2

The procedure of Comparison Example 1 was repeated except for replacing the hydroxypropylcellulose with the same amount of hydroxypropylmethylcellulose to obtain a fine powdery composition.

The powdery composition was analyzed by X-ray diffraction. A diffraction pattern was observed. Accordingly, it was confirmed that the 2-(2-dimethylaminobenzylsulfinyl)benzimidazole in the composition was in crystalline state.

Evaluation on Storage Stability

The 2-(2-dimethylaminobenzylsulfinyl)benzimidazole-containing compositions obtained in Examples were stored in a thermostat at 70° C. for 6 days. In the course of the storage, an amount of 2-(2-dimethylaminobenzylsulfinyl)benzimidazole remaining in the composition (i.e., remaining amount) was determined at lapse of 2 days, 4 days, and 6 days, to evaluate storage stability of 2-(2-dimethylaminobenzylsulfinyl)benzimidazole.

The remaining amount of 2-(2-dimethylaminobenzylsulfinyl)benzimidazole was determined by taking out approx. 900 mg of the stored sample, weighing the taken sample, adding methanol to the sample to make a total volume of precisely 100 ml under shaking for extraction by methanol, diluting the methanolic extract to make a total volume of 100 times as much as the methanolic extract, subjecting 20 μl of the diluted solution to determination based on HPLC (high pressure liquid chromatography) method.

The results are set forth in Table 1. The numerals in Table 1 mean relative amounts of the remaining 2-(2-dimethylaminobenzylsulfinyl)benzimidazole.

TABLE 1

| Sample | Period of Storage | | | |
|---|---|---|---|---|
| | 0 day | 2 days | 4 days | 6 days |
| Example 1 | 100 | 98.2 | 96.6 | 86.6 |
| Example 2 | 100 | 99.8 | 99.4 | 95.5 |
| Example 3 | 100 | 99.5 | 98.8 | 99.2 |
| Example 4 | 100 | 96.2 | 93.6 | 79.0 |
| Example 5 | 100 | 95.5 | 90.0 | 85.3 |
| Example 6 | 100 | 98.9 | 97.3 | 95.4 |
| Com. Ex. 1 | 100 | 94.8 | 87.2 | 56.2 |
| Com. Ex. 2 | 100 | 94.1 | 82.5 | 44.1 |

EXAMPLES 7–14

1.0 kg of the colorless 2-(2-dimethylaminobenzylsulfinyl)benzimidazole was pulverized by means of a jet mill 100AS (manufactured by Fuji Sangyo Co., Ltd.) at stream pressure of 5.5 kg/cm$^2$ and rate of 1 kg/hr to obtain a white microcrystalline 2-(2-dimethylaminobenzylsulfinyl)benzimidazole (decomposition point: 121°–127° C., mean diameter 2 μm) in 95% yield.

The microcrystalline 2-(2-dimethylaminobenzylsulfinyl)benzimidazole was mixed with a basic material set forth in Table 2 at weight ratio of 1:1. The resulting composition was stored at 50° C., 75% RH for 16 days, and then the remaining 2-(2-dimethylaminobenzylsulfinyl)benzimidazole was determined in the same manner described above.

The results are set forth in Table 2.

COMPARISON EXAMPLE 3

The procedure of Example 7 was repeated except that no basic material was mixed, to evaluate storage stability of the microcrystalline 2-(2-dimethylaminobenzylsulfinyl)benzimidazole. The result is set forth in Table 2.

COMPARISON EXAMPLES 4–11

The procedure of Example 7 was repeated except that the basic material was replaced with that set forth in Table 2, to evaluate storage stability of the microcrystalline 2-(2-dimethylaminobenzylsulfinyl)benzimidazole. The result is set forth in Table 2.

TABLE 2

| Sample | Added Material | Remaining amount (%) |
|---|---|---|
| Example 7 | Alumina magnesium hydroxide | 88.1 |
| Example 8 | Sodium carbonate | 94.7 |
| Example 9 | Calcium hydrogen phosphate | 95.8 |
| Example 10 | Aluminum hydroxide | 80.8 |
| Example 11 | Magnesium methasilicate aluminate | 51.1 |
| Example 12 | Anhydrous calcium phosphate | 97.4 |
| Example 13 | Magnesium carbonate | 78.9 |
| Example 14 | Sodium hydrogen carbonate | 81.2 |
| Com. Ex. 3 | — | 1.7 |
| Com. Ex. 4 | Calcium sulfate | 4.1 |
| Com. Ex. 5 | Lactose | 0.8 |
| Com. Ex. 6 | D-Mannitol | 0.9 |
| Com. Ex. 7 | Microcrystalline cellulose | 10.5 |
| Com. Ex. 8 | Corn starch | 3.0 |
| Com. Ex. 9 | Polyethylene glycol | 1.0 |
| Com. Ex. 10 | Methylcellulose | 1.4 |

TABLE 2-continued

| Sample | Added Material | Remaining amount (%) |
|---|---|---|
| Com. Ex. 11 | Succinic acid | 0.0 |

Remarks: The numerals in Table 2 mean relative amounts of the remaining 2-(2-dimethyl-aminobenzylsulfinyl)benzimidazole.

EXAMPLES 15–17

The procedure of Example 7 was repeated except that the basic material was replaced with that set forth in Table 3 and the storage period was changed to 30 days, to evaluate storage stability of the microcrystalline 2-(2-dimethylaminobenzylsulfinyl)benzimidazole. The results are set forth in Table 3.

TABLE 3

| Sample | Added Material | Remaining amount (%) |
|---|---|---|
| Example 15 | Alumina magnesium hydroxide | 51.6 |
| Example 16 | Aluminum hydroxide | 37.3 |
| Example 17 | Magnesium carbonate | 55.0 |

Remarks: The numerals in Table 3 mean relative amounts of the remaining 2-(2-dimethyl-aminobenzylsulfinyl)benzimidazole.

EXAMPLES 18 AND 19 AND COMPARISON EXAMPLES 12–13

The microcrylstalline 2-(2-dimethylaminobenzylsulfinyl)benzimidazole prepared in Example 7 was mixed with additives set forth in Table 4 to obtain a 2-(2-dimethylaminobenzylsulfinyl)benzimidazole-containing composition.

TABLE 4

| | Example | | Comparison |
|---|---|---|---|
| | 18 | 19 | Example 12 |
| Benzimidazole derivative | 30 | 30 | 30 |
| Lactose | 47 | 37 | 57 |
| Corn starch | 10 | 10 | 10 |
| Alumina magnesium hydroxide | 10 | 20 | — |
| Hydroxypropylcellulose | 3 | 3 | 3 |

In Table 4, the numerals are expressed in terms of weight parts.

The resulting compositions and an untreated microcrystalline 2-(2-dimethylaminobenzylsulfinyl)benzimidazole (for Comparison Example 13) were kept at 50° C., 75% RH for 5 days, 10 days and 20 days, for evaluating storage stability in the same manner as described above.

The results are set forth in Table 5. The numerals in Table 5 mean relative amounts of the remaining 2-(2-dimethylaminobenzylsulfinyl)benzimidazole.

TABLE 5

| Sample | Period of Storage | | | |
|---|---|---|---|---|
| | 0 day | 5 days | 10 days | 20 days |
| Example 18 | 100 | 99.6 | 95.2 | 93.4 |
| Example 19 | 100 | 99.6 | 94.8 | 92.9 |
| Com. Ex. 12 | 100 | 99.7 | 95.6 | 66.0 |
| Com. Ex. 13 | 100 | 95.1 | 1.6 | — |

EXAMPLES 20–22

1.0 kg of the colorless 2-(2-dimethylaminobenzylsulfinyl)benzimidazole was pulverized by means of a jet mill 100AS (manufactured by Fuji Sangyo Co., Ltd.) at stream pressure of 5.5 kg/cm$^2$ and rate of 1 kg/hr to obtain a white microcrystalline 2-(2-dimethylaminobenzylsulfinyl)benzimidazole (decomposition point: 121°–127° C., mean diameter 2 μm) in 95% yield.

The microcrystalline 2-(2-dimethylaminobenzylsulfinyl)benzimidazole was mixed with a basic material set forth in Table 6 at weight ratio of 1:1. The resulting composition was stored at 50° C., 75% RH for 16 days, and then the remaining 2-(2-dimethylaminobenzylsulfinyl)benzimidazole was determined in the same manner described above.

The results are set forth in Table 6.

TABLE 6

| Sample | Added Material | Remaining amount (%) |
|---|---|---|
| Example 20 | Nicotinamide | 64.6 |
| Example 21 | Magnesium stearate | 63.3 |
| Example 22 | Calcium stearate | 35.8 |

Remarks: The numerals in Table 6 mean relative amounts of the remaining 2-(2-dimethyl-aminobenzylsulfinyl)benzimidazole.

EXAMPLES 24 AND 24

The procedure of Example 1 was repeated except that the 2-(2-dimethylaminobenzylsulfinyl)benzimidazole was replaced with 2-(2-dimethylamino-5-methoxybenzyl)sulfinyl)benzimidazole (for Example 23) and 2-(2-dimethylamino-5-methylbenzylsulfinyl)-benzimidazole (for Example 24) and the amount of hydroxy propyl cellulose was changed into 5.0 g., to obtain an amorphous product. The test for evaluation of storage stability was performed in the same manner as described above except that the temperature and the storage period were changed to 60° C. and 10 days, respectively. The results are set forth in Tables 7 and 8.

EXAMPLES 25 AND 26

The procedure of Example 7 was repeated except that the 2-(2-dimethylaminobenzylsulfinyl)benzimidazole was replaced with 2-(dimethylamino-5-methoxybenzylsulfinyl)benzimidazole (for Example 25) and 2-(2-dimethylamino-5-methylbenzylsulfinyl)benzimidazole (for Example 26). The test for evaluation of storage stability was performed in the same manner as described above except that the temperature and the storage period were changed to 60° C. and 10 days, respectively. The results are set forth in Tables 7 and 8.

EXAMPLES 27 AND 28

The procedure of Example 21 was repeated except that the 2-(2-dimethylaminobenzylsulfinyl)benzimidazole was replaced with 2-(2-dimethylamino-5-methoxybenzylsulfinyl)benzimidazole (for Example 27) and 2-(2-dimethylamino-5-methylbenzylsulfinyl)benzimidazole (for Example 28). The test for evaluation of storage stability was performed in the same manner as described above except that the temperature and the storage period were changed to 60° C. and 10 days, respectively. The results are set forth in Tables 7 and 8.

COMPARISON EXAMPLES 14 AND 15

The procedure of Comparison Example 1 was repeated except that the 2-(2-dimethylaminobenzylsulfinyl)benzimidazole was replaced with 2-(2-dimethylamino-5-methoxybenzylsulfinyl)benzimidazole (for Comparison Example 14) and 2-(2-dimethylamino-5-methylbenzylsulfinyl)benzimidazole (for Comparison Example 15). The test for evaluation of storage stability was performed in the same manner as described above except that the temperature and the storage period were changed to 60° C. and 10 days, respectively. The results are set forth in Tables 7 and 8.

COMPARISON EXAMPLES 16 AND 17

The procedure of Comparison Example 5 was repeated except that the 2-(2-dimethylaminobenzylsulfinyl)benzimidazole was replaced with 2-(2-dimethylamino-5-methoxybenzylsulfinyl)benzimidazole (for Comparison Example 16) and 2-(2-dimethylamino-5-methylbenzylsulfinyl)benzimidazole (for Comparison Example 17). The test for evaluation of storage stability was performed in the same manner as described above except that the temperature and the storage period were changed to 60° C. and 10 days, respectively. The results are set forth in Tables 7 and 8.

COMPARISON EXAMPLES 18 AND 19

The procedure of Comparison Example 11 was repeated except that the 2-(2-dimethylaminobenzylsulfinyl)benzimidazole was replaced with 2-(2-dimethylamino-5-methoxybenzylsulfinyl)benzimidazole (for Comparison Example 18) and 2-(2-dimethylamino-5-methylbenzylsulfinyl)benzimidazole (for Comparison Example 19). The test for evaluation of storage stability was performed in the same manner as described above except that the temperature and the storage period were changed to 60° C. and 10 days, respectively. The results are set forth in Tables 7 and 8.

TABLE 7

| | [2-(2-dimethylamino-5-methoxybenzyl)sulfinylbenzimidazole] | | |
|---|---|---|---|
| | Storage Period | | |
| Sample | 0 day | 5 days | 10 days |
| Example 23 | 100 | 99.8 | 99.5 |
| Example 25 | 100 | 99.2 | 95.9 |
| Example 27 | 100 | 99.6 | 96.9 |
| Com. Ex. 14 | 100 | 98.3 | 74.6 |
| Com. Ex. 16 | 100 | 99.2 | 78.1 |
| Com. Ex. 18 | 100 | 0 | — |
| Ref. Ex. 1 | 100 | 99.4 | 76.3 |

Remarks: Sample of Ref. Ex. 1 is an untreated microcrystalline 2-(2-dimethylamino-5-methoxybenzyl-sulfinyl)benzimidazole. The numerals in Table 7 mean relative amounts of the remaining 2-(2-dimethylamino-5-methoxybenzylsulfinyl)benzimidazole.

TABLE 8

| | [2-(2-dimethylamino-5-methylbenzyl)sulfinylbenzimidazole] | | |
|---|---|---|---|
| | Storage Period | | |
| Sample | 0 day | 5 days | 10 days |
| Example 24 | 100 | 99.2 | 99.2 |
| Example 26 | 100 | 75.4 | 49.5 |
| Example 28 | 100 | 87.5 | 71.8 |
| Com. Ex. 15 | 100 | 9.9 | 4.5 |
| Com. Ex. 17 | 100 | 60.1 | 0.1 |
| Com. Ex. 19 | 100 | 0 | — |
| Ref. Ex. 2 | 100 | 30.4 | 10.0 |

Remarks: Sample of Ref. Ex. 2 is an untreated microcrystalline 2-(2-dimethylamino-5-methoxybenzyl-sulfinyl)benzimidazole. The numerals in Table 6 mean relative amounts of the remaining 2-(2-dimethylamino-5-methylbenzylsulfinyl)benzimidazole.

We claim:

1. A composition containing a physiologically active amorphous benzimidazole derivative having the formula (I):

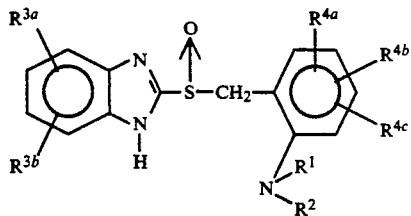 (I)

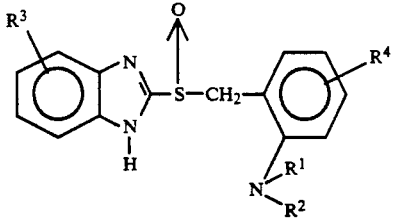 (II)

wherein $R^1$ is hydrogen atom, an alkyl group having 1 to 8 carbon atoms, a fluoroalkyl group having 1 to 6 carbon atoms, a cyclohexyl group, phenyl group or a benzyl group, $R^2$ is hydrogen atom or a lower alkyl group, or $R^1$ and $R^2$ together with the adjacent nitrogen atom form a piperidine, and each of $R^{3a}$, $R^{3b}$, $R^{4a}$, $R^{4b}$ and $R^{4c}$ independently is hydrogen atom, a halogen atom, a flouroalkyl group having 1 to 6 carbon atoms, a lower alkyl group, a lower alkoxy group, a lower alkoxycarbonyl group or an amino group, dispersed in an organic polymer wherein the organic polymer is selected from the group consisting of hydroxypropylcellulose, hydroxypropylmethylcellulose, methylcellulose, ethylcellulose, carboxymethylcellulose sodium, poly(vinylpyrrolidone), poly(vinyl alcohol), poly(sodium acrylate), sodium alginate, gelatin, gum arabic, α-starch, oxidized starch, heat-treated starch, enzyme-treated starch and agar and is contained in an amount of not less than 0.5 time as much as a weight of the benzimidazole derivative.

2. The composition as claimed in claim 1, wherein the benzimidazole derivative has the formula (II):

wherein $R^1$ is hydrogen atom, an alkyl group having 1 to 8 carbon atoms, a cyclohexyl group, phenyl group or a benzyl group, $R^2$ is hydrogen atom or a lower alkyl group, or $R^1$ and $R^2$ together with the adjacent nitrogen atom form a piperidine, and each of $R^3$ and $R^4$ independently is hydrogen atom, a halogen atom, trifluoromethyl group, a lower alkyl group, a lower alkoxy group, a lower alkoxycarbonyl group or an amino group.

3. The composition as claimed in claim 1, wherein the organic polymer is a cellulose derivative.

4. The composition as claimed in claim 1, wherein the organic polymer is water soluble polymer.

5. The composition as claimed in claim 1, wherein the organic polymer is contained in an amount of not less than 2 times as much as a weight of the benzimidazole derivative.

* * * * *